US005629329A

United States Patent [19]
Gray et al.

[11] Patent Number: 5,629,329
[45] Date of Patent: May 13, 1997

[54] METHODS FOR TREATING DISORDERS ASSOCIATED WITH THE CENTRAL NERVOUS SYSTEM USING OPTICALLLY PURE (+) CISAPRIDE

[75] Inventors: Nancy M. Gray, Marlborough, Mass.; James W. Young, Palo Alto, Calif.

[73] Assignee: Sepracor Inc., Marlborough, Mass.

[21] Appl. No.: 690,242

[22] Filed: Jul. 19, 1996

Related U.S. Application Data

[60] Division of Ser. No. 135,769, Oct. 12, 1993, which is a continuation-in-part of Ser. No. 909,841, Jul. 7, 1992, abandoned.

[51] Int. Cl.$^6$ .................. A61K 31/395; C07D 409/06
[52] U.S. Cl. .................. 514/327; 546/213; 546/221; 546/224
[58] Field of Search .................................. 514/327

[56] References Cited

U.S. PATENT DOCUMENTS

| | | | |
|---|---|---|---|
| 4,962,115 | 10/1990 | Van Daele | 514/326 |
| 5,057,525 | 10/1991 | Van Daele | 514/318 |
| 5,114,714 | 5/1992 | Young et al. | 424/400 |
| 5,114,715 | 5/1992 | Young et al. | 424/400 |
| 5,137,896 | 8/1992 | Van Daele | 514/327 |

FOREIGN PATENT DOCUMENTS

| | | |
|---|---|---|
| 0076530B1 | 4/1983 | European Pat. Off. . |
| WO-9401111 | 1/1994 | WIPO . |
| WO-9401112 | 1/1994 | WIPO . |

OTHER PUBLICATIONS

Jamali, F., "Enantioselective Aspects of Drug Action and Disposition Therapeutic Pitfalls," *Journal of Pharmaceutical Sciences*, 78(9):695–715 (1989).

Nemeth et al., *Chemical Abstracts*, vol. 111, No. 19, Abs. No. 167161a (1989).

Scrip's New Product Review No. 32 Cisapride, *PJB Publications Ltd.* (Apr. 1989).

Barnes, N.M., et al, "Identification of 5–HT$_3$ Recognition Sites in the Ferret Area Postrema," *J. Pharm. Pharmacol.*, 40:586–588 (1988).

Decktor, D.L., et al., "Effect of Metoclopramide, Bethanechol and the Cholecystokinin Receptor Antagonist, L–364, 718, on Gastric Emptying in the Rat," *Eur. J. Pharmacol.*, 147:313–316 (1988).

Lauwers, W., et al., "Identification of a Biliary Metabolite of Cisapride," *Biomedical and Environmental Mass Spectrometry*, 15:323–328 (1988).

Meuldermans, W., et al., "Excretion and Biotransformation of Cisapride in Dogs and Humans After Oral Administration," *Drug Metabolism and Disposition*, 16:3:403–419 (1988).

Van Peer, A., et al., "Clinical Pharmacokinetics of Cisapride," *Progress in the Treatment of Gastrointestinal Motility Disorders: The Role of Cisapride*, Proceedings of a Symposium in Frankfurt Excerpta Medica, pp. 23–29 (1988).

Barone et al., "Bioavailability of Three Oral Dosage Forms of Cisapride, a Gastrointestinal Stimulant Agent," *Clinical Pharmacy*, 6:640–645 (1987).

Costall, B., et al., "Emesis Induced by Cisplatin in the Ferret as a Model for the Detection of Anti–Emetic Drugs," *Neuropharmacology*, 26:1321–1326 (1987).

Stacher et al., "Effects of Oral Cisapride on Interdigestive Jejunal Motor Activity, Psychomotor Function, and Side–Effect Profile in Healthy Man," *Digestive Disease and Sciences*, 32:(11):1223–1230 (1987).

Fernandez & Massingham, "Peripheral Receptor Populations Involved in the Regulation of Gastrointestinal Motility and the Pharmacological Actions of Meoclopramide–like Drugs," *Life Sci.*, 36:1–14 (1985).

Schuurkes, J.A.J., et al., "Motor–Stimulating Properties of Cisapride on Isolated Gastrointestinal Preparations of the Guinea Pig," *J. Pharmacol. Exp. Ther.*, 234:775–783 (1985).

Williams & Burks, "Cisapride Increases Gastric Emptying Without Affecting Small or Large Bowel Transit," *Proc. West. Pharmacol. Soc.*, 28:47–50 (1985).

Milo, R., "Non–Cholinergic, Non–antidopaminergic Treatment of Chronic Digestive Symptoms Suggestive Of A Motility Disorder: A Two–Step Pilot Evaluation of Cisapride," *Curr. Therapeutic Research*, 36:5:1053–1062 (1984).

Reyntjens, A., et al., "Clinical Pharmacological Evidence For Cisapride's Lack of Antidopaminergic or Direct Cholinergic Properties," *Current Therapeutic Research*, 36:5:1045–1052 (1984).

Lavrijsen, K., et al., "The Role of CYP3A4 in the In–Vitro Metabolism of Cisapride in Human Liver Microsomes and In–Vitro and In–vivo Interactions of Cisapride with Co–Administered Drugs," *Dept. of Pharmacokinetics and Drug Metabolism, Janssen Research Foundation*.

Porsius, A.J., et al., "Farmacotoets 6A," *Farmacotherapie*, 129:9:214–217 (1994).

Schiavi, G.B., et al., "Identification of Serotonin 5–HT$_4$ Recognition Sites in the Porcine Caudate Nucleus by Radioligand Binding," *Neuropharmacology*, 33:543–549 (1994).

(List continued on next page.)

*Primary Examiner*—Robert T. Bond
*Attorney, Agent, or Firm*—Pennie & Edmonds

[57] ABSTRACT

Methods are disclosed utilizing the optically pure (+) isomer of cisapride. This compound is a potent drug for the treatment of gastro-esophageal reflux disease while substantially reducing the concomitant liability of adverse effects associated with the racemic mixture of cisapride. This compound is also useful in treating or preventing emesis while substantially reducing adverse effects associated with racemic cisapride. The optically pure (+) isomer of cisapride is also useful for the treatment of dyspepsia and such other conditions as may be related to the activity of (+) cisapride as a prokinetic agent, such as gastroparesis, constipation, postoperative ileus, and intestinal pseudo-obstruction, without the concomitant liability of adverse effects associated with the racemic mixture of cisapride. The (+) isomer of cisapride also exhibits longer duration of action than does racemic cisapride and is useful for treatment of disorders of the central nervous system.

8 Claims, No Drawings

OTHER PUBLICATIONS

Krejs, G.J., "Sérotonine intestinale, une cible thérapeutique," *Méd. Chir. Dig.*, 22:7:415–416 (1993).

Zuccato, E., et al., "The Effects of S(–) and (+) Sulpiride, Metoclopramide, Cisapride and Domperidone on the Small Intestine Suggest $DA_2$-Receptors are Involved in the Control of Small Intestinal Transit Time in Rats," *Pharmacological Research*, 26:2:179–185 (1992).

Gladziwa, U., et al., "Pharmacokinetics and pharmacodynamics of cisapride in patients undergoing hemodialysis," *Clinical Pharmacology*, 50:6:673–681 (1991).

Frazer, A., et al., "Subtypes of Receptors for Serotonin," *Annual Rev. of Pharmacology and Toxicology*, 30:307–348 (1990).

Schapira, M., et al., "The Current Status of Gastric Prokinetic Drugs," *Acta Gastroenterolog. Belg.* LIII:446–457 (1990).

Clarke, D.E., et al., "The $5-HT_3$ Receptor: Naughty, but Nice," *Trends in Pharmacological Sciences*, 10:385–386 (1989).

Craig & Clark, "5–Hydroxytryptamine and Cholinergic Mechanisms in Guinea–pig Ileum," *Brit. J. Pharmacol.*, 96:247 (1989).

Dumuis, A., et al., "The Gastrointestinal Prokinetic Benzamide Derivatives are Agonist at the Non–Classical 5–HT Receptor ($5-HT_4$) Positively Coupled to Adenylate Cyclase in Neurons," *N.S. Arch. Pharmacol.*, 340:403–410 (1989).

Gullikson, G.W., et al., "Relationship of Serotonin–3 Receptor Antagonist Activity to Gastric Emptying and Motor–Stimulating Actions of Prokinetic Drugs in Dogs," *Journal of Pharmacology and Experimental Therapeutics*, 258(1):103–110 (1991).

Nemeth, P.R. and Gullikson, G.W., "Gastrointestinal Motility Stimulating Drugs and 5–HT Receptors on Myenteric Neurons," *European Journal of Pharmacology*, 166:387–391 (1989).

Meuldermans, W., et al., "Excretion and Biotransformation of Cisapride in Rats After Oral Administration," *Drug Metabolism and Disposition*, 16:3:410–419 (1988).

Van Daele, G.H.P., et al., "Synthesis of Cisapride, a Gastrointestinal Stimulant Derived From Cis–4–Amino–3–Methoxypiperdine," *Drug Development Research*, 8:225–232 (1986).

METHODS FOR TREATING DISORDERS ASSOCIATED WITH THE CENTRAL NERVOUS SYSTEM USING OPTICALLLY PURE (+) CISAPRIDE

This application is a division of application Ser. No. 08/135,769, filed Oct. 12, 1993 and which in turn is a continuation-in-part of application Ser. No. 07/909,841, filed Jul. 7, 1992, now abandoned.

1. TECHNICAL FIELD

This invention relates to novel compositions of matter containing optically pure (+) cisapride. These compositions possess potent activity in treating gastro-esophageal reflux disease while substantially reducing adverse effects associated with the administration of the racemic mixture of cisapride including but not limited to diarrhea, abdominal cramping and elevations of blood pressure and heart rate. Additionally, these novel compositions of matter containing optically pure (+) cisapride are useful in treating emesis and such other conditions as may be related to the activity of (+) cisapride as a prokinetic agent, including but not limited to dyspepsia, gastroparesis, constipation, and intestinal pseudo-obstruction, while substantially reducing adverse effects associated with the administration of the racemic mixture of cisapride. Also disclosed are methods for treating the above-described conditions in a human while substantially reducing adverse effects that are associated with the racemic mixture of cisapride, by administering the (+) isomer of cisapride to a human in need of such treatment.

The active compound of these compositions and methods is an optical isomer of racemic cis-cisapride, which is described in European Patent Application No. 0,076,530 A2 published Apr. 13, 1983 and U.S. Pat. Nos. 4,962,115 and 5,057,525. Chemically, the active compound, of the presently disclosed compositions and methods, is the (+) isomer of cis-4-amino-5-chloro-N-[1-[3-(4-fluorophenoxy) propyl]-3-methoxy-4-piperidinyl]-2-methoxybenzamide, hereinafter referred to as (+) cisapride. The term "(+) isomer of cisapride" and particularly the term "(+) cisapride" encompass optically pure and substantially optically pure (+) cisapride. Similarly, as used herein, the terms "racemic cisapride" or "racemic mixture of cisapride" refer to the cis diastereomeric racemate.

Cisapride, which is the subject of the present invention, is available commercially only as the 1:1 racemic mixture of the cis diastereomeric racemate. Cisapride is available only as a mixture of optical isomers, called enantiomers, i.e., a mixture of cis(+) and cis(−) cisapride.

2. BACKGROUND OF THE INVENTION

2.1 Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen.

2.2 Pharmacologic Action

U.S. Pat. Nos. 4,962,115 and 5,057,525 (collectively "Van Daele") disclose N-(3-hydroxy-4-piperidenyl)benzamides including the cis and trans diastereomeric racemates of cisapride. Van Daele discloses that these compounds, the pharmaceutically acceptable acid addition salts thereof and the stereochemically isomeric forms thereof, stimulate the motility of the gastro-intestinal system. Van Daele states that the diastereomeric racemates of these compounds may be obtained separately by conventional methods and that these diastereomeric racemates may be further resolved into their optical isomers. Van Daele also reports the "lowest effective concentration . . . whereby a significant stimulation of the acetylcholine release is noted", for cis(+) and cis(−) cisapride, to be 0.01 mg/L and 0.04 mg/L respectively, while the "lowest effective dose whereby antagonistic effects of dopamine-induced gastric relaxation are observed" is reported to be 0.63 mg/L for both cis(+) and cis(−) cisapride. Therefore, Van Daele teaches that cis(+) and cis(−) cisapride have roughly identical pharmacological profiles.

Cisapride is one of a class of compounds known as benzamide derivatives, the parent compound of which is metoclopramide (See: Schapira et al., *Acta Gastro-Enterolog. Belg.* LIII: 446–457, 1990). As a class, these benzamide derivatives have several prominent pharmacological actions. The prominent pharmacological activities of the benzamide derivatives are due to their effects on the neuronal systems which are modulated by the neurotransmitter serotonin. The role of serotonin, and thus the pharmacology of the benzamide derivatives, has been broadly implicated in a variety of conditions for many years (See Phillis, J. W., *"The Pharmacology of Synapses"*, Pergamon Press, Monograph 43, 1970; Frazer, A. et al., *Annual Rev. of Pharmacology and Therapeutics* 30: 307–348, 1990). Thus, research has focused on locating the production and storage sites of serotonin as well as the location of serotonin receptors in the human body in order to determine the connection between these sites and various disease states or conditions.

In this regard, it was discovered that a major site of production and storage of serotonin is the enterochromaffin cell of the gastrointestinal mucosa. It was also discovered that serotonin has a powerful stimulating action on intestinal motility by stimulating intestinal smooth muscle, speeding intestinal transit, and decreasing absorption time, as in diarrhea. This stimulating action is also associated with nausea and vomiting.

Because of their modulation of the serotonin neuronal system in the gastrointestinal tract, many of the benzamide derivatives are effective antiemetic agents and are commonly used to control vomiting during cancer chemotherapy or radiotherapy, especially when highly emetogenic compounds such as cisplatin are used (See: Costall et al.,

*Neuropharmacology* 26: 1321–1326,1987). This action is almost certainly the result of the ability of the compounds to block the actions of serotonin (5HT) at specific Sites of action, called the 5HT3-receptor, which was classically designated in the scientific literature as the serotonin M-receptor (See: Clarke et al., *Trends in Pharmacological Sciences* 10: 385–386, 1989). Chemo- and radio-therapy may induce nausea and vomiting by the release of serotonin from damaged enterochromaffin cells in the gastrointestinal tract. Release of the neurotransmitter serotonin stimulates both afferent vagal nerve fibers (thus initiating the vomiting reflex) and serotonin receptors in the chemoreceptor trigger zone of the area postrema region of the brain. The anatomical site for this action of the benzamide derivatives, and whether such action is central (CNS), peripheral, or a combination thereof, remains unresolved (See: Barnes et al., *J. Pharm. Pharmacol.* 40: 586–588, 1988). Cisapride, like the other benzamide derivatives may be an effective antiemetic agent based on its ability to modulate the activity of serotonin at the 5HT3 receptor.

A second prominent action of the benzamide derivatives is in augmenting gastrointestinal smooth muscle activity from the esophagus through the proximal small bowel, thus accelerating esophageal and small intestinal transit as well as facilitating gastric emptying and increasing lower esophageal sphincter tone (See: Decktor et al., *Eur. J. Pharmacol.* 147: 313–316, 1988). Although the benzamide derivatives are not cholinergic receptor agonists per se, the aforementioned smooth muscle effects may be blocked by muscarinic receptor blocking agents such as atropine or neuronal transmission inhibitors of the tetrodotoxin type which affect sodium channels (See: Fernandez and Massingham, *Life Sci.* 36: 1–14, 1985). Similar blocking activity has been reported for the contractile effects of serotonin in the small intestine (See: Craig and Clarke, *Brit. J. Pharmacol.* 96: 247 P, 1989). It is currently believed that the primary smooth muscle effects of the benzamide derivatives are the result of an agonist action upon a new class of serotonin receptors referred to as 5HT4 receptors which are located on interneurons in the myenteric plexus of the gut wall (See Clarke et al., *Trends in Pharmacological Sciences* 10: 385–386, 1989 and Dumuis et al., *N. S. Arch. Pharmacol.* 340: 403–410, 1989). Activation of these receptors subsequently enhances the release of acetylcholine from parasympathetic nerve terminals located near surrounding smooth muscle fibers, and it is the combination of acetylcholine with its receptors on smooth muscle membranes which is the actual trigger for muscle contraction.

Racemic cisapride possesses similar properties to metoclopramide except that it lacks dopamine receptor blocking activity (See: Reyntjens et al., *Curr. Therap. Res.* 36: 1045–1046, 1984) and enhances motility in the colon as well as in the upper portions of the alimentary tract (See: Milo, *Curr. Therap. Res.* 36: 1053–1062, 1984). The colonic effects, however, may not be completely blocked by atropine and may represent, at least in part, a direct action of the drug (See: Schuurkes et al., *J. Pharmacol Exp. Ther.* 234: 775–783, 1985). Using cultured mouse embryo colliculi neurons and cAMP generation as an endpoint for designating 5HT4 activity, the EC50 concentration of racemic cisapride was $7 \times 10^{-8}$ M (See: Dumuis et al., *N. S. Arch. Pharmacol.* 340: 403–410, 1989). Drugs of this class do not affect gastric acid secretion and have variable effects upon colonic motility (See: Reyntjens et al., *Curr. Therap. Res.* 36: 1045–1046, 1984 and Milo, *Curr. Therap. Res.* 36: 1053–1062, 1984).

The racemic mixture of cisapride is presently used primarily to treat gastro-esophageal reflux disease. This disease is characterized as the backward flow of the stomach contents into the esophagus. One of the most important factors in the pathogenesis of gastro-esophageal reflux disease is a reduction in the pressure barrier due to the failure of the lower esophageal sphincter. Failure of the lower esophageal sphincter can arise due to a low basal pressure, sphincter relaxation, or to a non-compensated increase in intragastric pressure. Other factors in the pathogenesis of the disease are delayed gastric emptying, insufficient esophageal clearing due to impaired peristalsis and the corrosive nature of the reflux material which can damage esophageal mucosa. The racemic mixture of cisapride is thought to strengthen the anti-reflux barrier and improve esophageal clearance by increasing the lower esophageal sphincter pressure and enhancing peristaltic contractions.

Because of its activity as a prokinetic agent, the racemic mixture of cisapride may also be useful to treat dyspepsia, gastroparesis, constipation, post-operative ileus, and intestinal pseudo-obstruction. Dyspepsia is a condition characterized by an impairment of the power or function of digestion that can arise as a symptom of a primary gastrointestinal dysfunction or as a complication due to other disorders such as appendicitis, gallbladder disturbances, or malnutrition. Gastroparesis is a paralysis of the stomach brought about by a motor abnormality in the stomach or as a complication of diseases such as diabetes, progressive systemic sclerosis, anorexia nervosa or myotonic dystrophy. Constipation is a condition characterized infrequent or difficult evacuation of feces resulting from conditions such as lack of intestinal muscle tone or intestinal spasticity. Postoperative ileus is an obstruction in the intestine due to a disruption in muscle tone following surgery. Intestinal pseudo-obstruction is a condition characterized by constipation, colicky pain, and vomiting, but without evidence of physical obstruction.

The administration of the racemic mixture of cisapride to a human has been found to cause adverse effects including, tachycardia, CNS disorders, increased systolic pressure, interactions with other drugs, diarrhea, and abdominal cramping. Further, it has been reported that intravenous administration of racemic cisapride demonstrates the occurrence of additional adverse (side) effects not experienced after oral administration of racemic cisapride. Stacher et al. *Digestive Diseases and Sciences* 32(11): 1223–1230 (1987).

Racemic cisapride is almost completely absorbed after oral administration to humans, but the bioavailability of the parent compound is only 40–50%, due to rapid first pass metabolism in the liver (See: Van Peer et al., in *Progress in the Treatment of Gastrointestinal Motility Disorders: The Role of Cisapride.* Proceedings of a Symposium in Frankfurt. November 1986. Johnson A. G. and Lux, G. eds. Excerpta Medica, Amsterdam, pp. 23–29 (1988). More than 90% of a dose of cisapride is metabolized mainly by oxidative N-dealkylation at the piperidine nitrogen or by aromatic hydroxylation occurring on either the 4-fluorophenoxy or benzamide rings. Short duration of action, as seen with racemic cisapride, can often be associated with erratic pharmacological effects following oral administration of compounds.

Thus, it would be particularly desirable to find a compound with the advantages of the racemic mixture of cisapride which would not have the aforementioned disadvantages.

3. SUMMARY OF THE INVENTION

It has now been discovered that novel compositions of matter containing the optically pure (+) isomer of cisapride are useful in treating gastro-esophageal reflux disease while substantially reducing adverse effects associated with the administration of the racemic mixture of cisapride, including but not limited to diarrhea, abdominal cramping and elevations of blood pressure and heart rate. It has also been discovered that optically pure (+) cisapride is an effective antiemetic agent, useful as an adjunctive therapy in cancer treatment to alleviate nausea and vomiting induced by chemo- or radio-therapeutics, while substantially reducing the above-described adverse effects associated with the administration of the racemic mixture of cisapride. It has also been discovered that these novel compositions of matter containing optically pure (+) cisapride are useful in treating dyspepsia and such other conditions as may be related to the activity of (+) cisapride as a prokinetic agent, e.g., gastroparesis, constipation, post-operative ileus, and intestinal pseudo-obstruction, while substantially reducing the above-described adverse effects associated with the administration of the racemic mixture of cisapride. The present invention also includes methods for treating the above-described conditions in a human while substantially reducing adverse effects that are associated with the racemic mixture of cisapride, by administering the optically pure (+) isomer of cisapride to said human. Furthermore, the present invention also includes methods and compositions which demonstrate an improved bioavailability over racemic cisapride irrespective of the mode of administration.

4. DETAILED DESCRIPTION OF THE INVENTION

The present invention encompasses a method of treating gastro-esophageal reflux disease in a human, while substantially reducing the concomitant liability of adverse effects associated with the administration of racemic cisapride, which comprises administering to a human in need of such treatment, an amount of (+) cisapride, or a pharmaceutically acceptable salt thereof, substantially free of its (−) stereoisomer, said amount being sufficient to alleviate said reflux disease, but insufficient to cause said adverse effects associated with the racemic mixture of cisapride.

The present invention also encompasses a composition for the treatment of a human suffering from gastro-esophageal reflux disease, which comprises an amount of (+) cisapride, or a pharmaceutically acceptable salt thereof, substantially free of its (−) stereoisomer, said amount being sufficient to alleviate said reflux disease, but insufficient to cause adverse effects associated with racemic cisapride.

The present invention further encompasses a method of eliciting an antiemetic effect in a human, while substantially reducing the concomitant liability of adverse effects associated with the administration of racemic cisapride, which comprises administering to a human in need of such antiemetic therapy, an amount of (+) cisapride, or a pharmaceutically acceptable salt thereof, substantially free of its (−) stereoisomer, said amount being sufficient to alleviate nausea and vomiting but insufficient to cause adverse effects associated with the administration of racemic cisapride.

In addition, the present invention encompasses an antiemetic composition for the treatment of a human in need of antiemetic therapy, which comprises an amount of (+) cisapride, or a pharmaceutically acceptable salt thereof, substantially free of its (−) stereoisomer, said amount being sufficient to alleviate nausea and vomiting but insufficient to cause adverse effects associated with the administration of racemic cisapride.

A further aspect of the present invention includes a method of treating a condition caused by gastrointestinal motility dysfunction in a human, while substantially reducing the concomitant liability of adverse effects associated with the administration of racemic cisapride, which comprises administering to a human in need of treatment for gastrointestinal motility dysfunction, an amount of (+) cisapride, or a pharmaceutically acceptable salt thereof, substantially free of its (−) stereoisomer, said amount being sufficient to alleviate said condition but insufficient to cause adverse effects associated with the administration of racemic cisapride. Conditions caused by gastrointestinal motility dysfunction in a human include, but are not limited to, dyspepsia, gastroparesis, constipation, post-operative ileus, and intestinal pseudo-obstruction.

Furthermore, the present invention includes a composition for treating a condition caused by gastrointestinal motility dysfunction in a human, which comprises an amount of (+) cisapride, or a pharmaceutically acceptable salt thereof, substantially free of its (−) stereoisomer, said amount being sufficient to alleviate said condition caused by gastrointestinal motility dysfunction, but insufficient to cause adverse effects associated with the administration of racemic cisapride.

The present invention encompasses a novel composition of matter comprising (+) cisapride or a pharmaceutically acceptable salt thereof, substantially free of its (−) stereoisomer, wherein said composition provides a higher bioavailability of the active compound than does the racemic mixture. The bioavailability of (+) cisapride is found to be higher than that of racemic cisapride irrespective of the mode of administration. Further, these novel compositions are used to treat a variety of disorders, as described above, while substantially reducing adverse effects which are caused by the administration of racemic cisapride. These novel compositions may optionally contain a pharmaceutically acceptable carrier or combinations thereof as described below.

The increased bioavailability of (+) cisapride allows for a more effective pharmacodynamic profile than racemic cisapride and a more effective management of the disease being treated. For example, a more effective management of disorders is achieved with the administration of (+) cisapride, since dosing frequency can be reduced. This would facilitate, e.g., overnight treatment while the patient is asleep. Similarly, a lower dose frequency is beneficial when (+) cisapride is used prophylactically or as a treatment for emesis in cancer patients.

Therefore, the present invention further encompasses a method for treating gastro-esophageal reflux disease in a human while achieving higher bioavailability than racemic cisapride which comprises administering to a human in need of treatment from such a disorder, an amount of (+) cisapride, or a pharmaceutically acceptable salt thereof, substantially free of its (−) stereoisomer, said amount being sufficient to alleviate said reflux disease and said amount having increased bioavailability over the racemic mixture of cisapride.

The present invention also encompasses a method of eliciting an antiemetic effect in a human while achieving a higher bioavailability than racemic cisapride which comprises administering to a human in need of antiemetic therapy, an amount of (+) cisapride, or a pharmaceutically acceptable salt thereof, substantially free of its (−) stereoisomer, said amount being sufficient to alleviate nausea and vomiting and said amount having higher bioavailability than racemic cisapride.

The present invention further encompasses a method of treating a condition caused by gastro-intestinal motility dysfunction in a human, while achieving higher bioavailability than racemic cisapride, which comprises administering to a human in need of treatment for gastrointestinal motility dysfunction, an amount of (+) cisapride, or a pharmaceutically acceptable salt thereof, substantially free of its (−) stereoisomer, said amount being sufficient to alleviate said condition and said amount having a higher bioavailability than racemic cisapride.

In addition, the present invention encompasses methods for treating the above-described conditions, comprising administering to a human in need of treatment for such a condition, an amount of (+) cisapride, or a pharmaceutically acceptable salt thereof, substantially free of its (−) stereoisomer, said amount having increased bioavailability over the racemic mixture and being sufficient to alleviate said condition but being insufficient to cause adverse effects associated with racemic cisapride.

The observation that cisapride enters the central nervous system and binds to 5HT4 receptors indicates that cisapride may have centrally-mediated effects. As was shown by Dumuis et al., N.S. Arch. Pharmacol. 340: 403–410, 1989, cisapride is a potent ligand at 5HT4 receptors, and these receptors are located in several areas of the central nervous system. Modulation of serotonergic systems has a variety of behavioral effects. Cisapride, therefore, could be therapeutically useful in the treatment of: 1) cognitive disorders, including but not limited to Alzheimer's disease; 2) behavioral disorders, including but not limited to schizophrenia, mania, obsessive-compulsive disorder, and psychoactive substance use disorders; 3) mood disorders, including but not limited to depression and anxiety; and 4) disorders of control of autonomic function, including but not limited to essential hypertension and sleep disorders.

The available racemic mixture of cisapride (i.e., a 1:1 racemic mixture of the two cis enantiomers) possesses prokinetic and antiemetic activity, and provides therapy and a reduction of symptoms in a variety of conditions and disorders related to gastrointestinal motility dysfunction; however, this racemic mixture, while offering the expectation of efficacy, causes adverse effects and has a relatively short duration of action. Utilizing the substantially optically pure or optically pure isomer of (+) cisapride results in clearer dose related definitions of efficacy, diminished adverse effects, and accordingly, an improved therapeutic index as well as a higher bioavailability. It is therefore more desirable to use the (+) isomer of cisapride than to administer the racemic mixture.

The term "bioavailability" refers to the rate, extent, and duration with which an active drug or metabolite enters and remains in the general circulation, thereby permitting access to the site of action. Higher bioavailability may be achieved by, e.g., increasing the drug's duration of action.

The term "adverse effects" includes, but is not limited to, gastrointestinal disorders such as diarrhea, abdominal cramping, and abdominal grumbling; tiredness; headache; increased systolic pressure; increased heart rate; neurological and CNS disorders; and interaction of cisapride with other drug given concurrently such as digoxin, diazepam, ethanol, acenocoumarol, cimetidine, ranitidine, paracetamol, and propranolol.

The term "substantially free of its (−) stereoisomer" as used herein means that the compositions contain at least 90% by weight of (+) cisapride and 10% by weight or less of (−) cisapride. In a more preferred embodiment the term "substantially free of the (−) stereoisomer" means that the composition contains at least 99% by weight of (+) cisapride, and 1% or less of (−) cisapride. In a most preferred embodiment, "the term substantially free of its (−) stereoisomer" as used herein means that the composition contains greater than 99% by weight of (+) cisapride. These percentages are based upon the total amount of cisapride in the composition. The terms "substantially optically pure (+) isomer of cisapride" or "substantially optically pure (+) cisapride" and "optically pure (+) isomer of cisapride" and "optically pure (+) cisapride" are encompassed by the above-described amounts.

The term "gastro-esophageal reflux disease" as used herein means the incidence of, and the symptoms of, those conditions causing the backward flow of the stomach contents into the esophagus.

The terms "eliciting an antiemetic effect" and "antiemetic therapy" as used herein mean providing relief from or preventing the symptoms of nausea and vomiting induced spontaneously or associated with emetogenic cancer chemotherapy or irradiation therapy.

The term "treating a condition caused by gastrointestinal motility dysfunction" as used herein means treating the symptoms and conditions associated with this disorder which include, but are not limited to, dyspepsia, gastroparesis, constipation, post-operative ileus, and intestinal pseudo-obstruction.

The term "prokinetic" as used herein means the enhancement of peristalsis in, and thus the movement through the gastrointestinal tract.

The term "dyspepsia" as used herein means a condition characterized by an impairment of the power or function of digestion that can arise as a symptom of a primary gastrointestinal dysfunction or as a complication due to other disorders such as appendicitis, gallbladder disturbances, or malnutrition.

The term "gastroparesis" as used herein means a paralysis of the stomach brought about by a motor abnormality in the stomach or as a complication of diseases such as diabetes, progressive systemic sclerosis, anorexia nervosa, or myotonic dystrophy.

The term "constipation" as used herein means a condition characterized by infrequent or difficult evacuation of feces resulting from conditions such as lack of intestinal muscle tone or intestinal spasticity.

The term "post-operative ileus" as used herein means an obstruction in the intestine due to a disruption in muscle tone following surgery.

The term "intestinal pseudo-obstruction" as used herein means a condition characterized by constipation, colicky pain, and vomiting, but without evidence of physical obstruction.

The chemical synthesis of the racemic mixture of cisapride can be performed by the method described in European Patent Application No. 0,076,530 A2 published Apr. 13, 1983, U.S. Pat. Nos. 4,962,115 and 5,057,525 and in Van Daele et al., Drug Development Res. 8: 225–232 (1986), the disclosures of which are incorporated herein by reference. The (+) isomer of cisapride may be obtained from its racemic mixture by resolution of the enantiomers using conventional means such as from an optically active resolving acid. See, for example, "Enantiomers, Racemates and Resolutions," by J. Jacques, A. Collet, and S. H. Wilen, (Wiley-Intenscience, New York, 1981); S. H. Wilen, A. Collet, and J. Jacques, Tetrahedron, 33, 2725 (1977); and "Stereochemistry of Carbon Compounds, by E. L. Eliel (McGraw-Hill, N.Y., 1962) and S. H. Wilen, page 268, in "Tables of Resolving Agents and Optical Resolutions" (E. L. Eliel, Ed. Univ. of Notre Dame Press, Notre Dame, Ind., 1972). Furthermore, the optically pure (+) isomer of cisapride can be prepared from the racemic mixture by enzymatic biocatalytic resolution. See, for example, U.S. Pat. Nos. 5,057,427 and 5,077,217, the disclosures of which are incorporated by reference.

The magnitude of a prophylactic or therapeutic dose of (+) cisapride in the acute or chronic management of diseases and/or disorders described herein will vary with the severity of the condition to be treated, and the route of administration. The dose, and perhaps the dose frequency, will also vary according to the age, body weight, and response of the individual patient. In general, the total daily dose range for (+) cisapride, for the conditions described herein, is from about 1 mg to about 200 mg, in single or divided doses. Preferably, a daily dose range should be between about 5 mg to about 100 mg, in single or divided doses, while most preferably, a daily dose range should be between about 5 mg to about 75 mg, in single or divided doses. It is preferred that the doses are administered from 1 to 4 times a day. In managing the patient, the therapy should be initiated at a lower dose, perhaps about 5 mg to about 10 mg, and increased up to about 50 mg or higher depending on the patient's global response. It is further recommended that children, and patients over 65 years, and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The terms an "amount sufficient to alleviate said reflux disease, but insufficient to cause adverse effects", "an amount sufficient to alleviate nausea and vomiting but insufficient to cause adverse effects", "and an amount sufficient to alleviate said condition caused by gastrointestinal motility dysfunction, but insufficient to cause adverse effects" are encompassed by the above-described dosage amounts and dose frequency schedule.

Any suitable route of administration may be employed for providing the patient with an effective dosage of cisapride. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise (+) cisapride as the active ingredient, or a pharmaceutically acceptable salt thereof, and may also contain a pharmaceutically acceptable carrier, and optionally, other therapeutic ingredients The term "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Preferred acid addition salts are the chloride and sulfate salts. In the most preferred embodiment, (+) cisapride is administered as the free base.

The compositions of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets) with the oral solid preparations being preferred over the oral liquid preparations. A preferred oral solid preparation is capsules. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, or tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet contains from about 1 mg to about 100 mg of the active ingredient, and each cachet or capsule contains from about 1 mg to about 50 mg of the active ingredient. Most preferably, the tablet, cachet or capsule contains either one of three dosages, i.e., about 5 mg, about 10 mg or about 25 mg of the active ingredient.

The invention is further defined by reference to the following examples, describing in detail the preparation of the compound and the compositions of the present invention, as well as their utility. It will be apparent to those skilled in the art that many modifications, both to materials and methods, may be practiced without departing from the purpose and interest of this invention.

5. EXAMPLES

5.1 Example 1

Determination of Efficacy

The relative activities of optically pure (−), (+), and racemic cisapride are determined by a pharmacological study in dogs. Evaluation of these compounds is based on their relative potencies in a test to measure gastric emptying as an index of prokinetic activity in the stomach. The compounds are dissolved or suspended in 0.5% methylcellulose and administered at varying doses via an indwelling gastric fistula to adult beagle dogs. The compounds are given 60 minutes prior to the administration via fistula of a liquid test meal containing the dye phenol red. The gastric contents are collected 5 minutes later via gravity drainage through the fistula. Gastric emptying during this period may be calculated according to the formula of Debas (See: Fitzpatrick et al., *J. Pharmacol. Exp. Ther.* 254: 450–455, 1990) which takes into account both the volume of meal collected and the concentration of the dye. The relative potencies of (−) cisapride, (+) cisapride, and racemic cisapride are assessed via standard parallel line assays.

5.2 Example 2

Bioavailability

A single dose of test substance or vehicle is administered to male beagle dogs either intravenously as a bolus over one minute using a 23 ga butterfly needle into the saphenous vein, or as a single dose via oral gavage. 2.0 ml of whole blood is collected from each dog prior to and at intervals of 0.083, 0.25, 0.5, 1, 2, 3, 4, 6, 9, 12, and 24 hours following the intravenous or oral administration of (+), (−), or racemic cisapride. The dogs are placed in sling-restraint prior to administration of test substance and are transferred to metabolic cages following collection of the 0.083 hour blood sample. All blood samples are collected from an angiocatheter placed in a cephalic vein on the morning of the experiment.

The blood is drawn into a 3 cc syringe. The first 1.0–2.0 ml of blood is discarded. The next 2.0 ml of whole blood is quickly transferred to a heparinized tube. The heparinized tubes are kept on ice until the blood is added. After adding the blood to the tube, the contents of the tube are mixed and centrifuged to obtain plasma. The plasma is carefully decanted and transferred to a test tube labelled with: the animal number, the dose of test substance administered, the route of administration, the date of administration, and the time of blood collection. The tubes are stored at −20° C. until analysis.

Analysis of the concentration of (+), (−), or racemic cisapride in each plasma sample is determined using high performance liquid chromatography. For each test substance the plasma concentration vs. sample time is plotted for both routes of administration. The oral bioavailability of each test substance is determined by comparing the $C_{max}$ and AUC for the oral route of administration versus those for the i.v. route. The $t_{1/2}$ for each test substance by both routes is calculated as an indicator of duration of action.

5.3 Example 3

5HT3 Receptor Binding

The affinity of compounds for the 5HT3 receptor is assessed via a radioligand binding assay using animal membranes that are rich in such receptors, e.g., those derived from the cerebral cortex of rat brains (See: Fitzpatrick et al., *J. Pharmacol. Exp. Ther.* 254: 450455, 1990). Plasma membranes from the animal source are equilibrated in test tubes with solutions containing a radioactive 5HT3 receptor ligand and various concentrations of (−) cisapride, (+) cisapride or racemic cisapride. After incubation for 30 minutes, the membranes are isolated on a filter and the degree of inhibition of radioactive ligand binding is determined. Based on the results obtained, the concentration of each compound which inhibits ligand binding by 50% (the IC50) is calculated.

5.4 Example 4

5HT4 Receptor Agonist Activity

Agonist activity at 5HT4 receptor sites is assessed using an assay based on the ability of active compounds to increase cyclic AMP production in mouse embryo colloculi neurones grown in tissue culture (See: Dumuis et al., *N. S. Arch. Pharmacol.* 340: 403–410, 1989). (−) cisapride, (+) cisapride and racemic cisapride, at varying concentrations, are incubated with these cells for 10 minutes in the presence of the cAMP precursor substance, ATP. At the end of this period, the degree of formation of cAMP is assessed. The concentration of agonist compound required to increase the formation of cAMP by 50% of the maximal possible (the EC50) is then calculated.

5.5 Example 5

Determination of Cardiovascular Effects

Unanesthetized spontaneously hypertensive rats (SHR) with systolic blood pressures ranging between 180 and 220 mm Hg are used. Blood pressure is recorded indirectly in a temperature-controlled environment before, and 1, 2, and 4 hours after, the test substance is administered p.o. The test substances are racemic, (−) and (+) cisaprid. Increases in-systolic blood pressure by more than 10% (>10) at any two of the aforementioned three consecutive time points is considered significant. In the same spontaneously hypertensive rats, heart rate is recorded by a cardiograph immediately after the blood pressure recordings. An increase in heart rate greater than 20 percent (>20) from pre-treatment control readings is considered significant.

5.6 Example 6

Colonic Propulsive Motility

The purpose of this study is to demonstrate and characterize the pharmacological effects of experimental compounds on colonic propulsive motility in the mouse. The test is based on the reflex expulsion of a glass bead from the distal colon, which is indicative of drug effects on the reflex arc. This test is useful in evaluating whether diarrhea is a side effect, and may provide evidence of compounds lacking this effect.

Female albino Swiss CD-1 mice, 18–24 grams, are obtained. They are housed in groups of 5–10 in plastic cages maintained in a climate-controlled room with water and food available ad libitum. Mice are fasted for one hour prior to oral administration of test compounds. Mice are administered drug (calculated as base weight) or vehicle by the appropriate route. Control animals receive a similar quantity of the appropriate vehicle.

The experimental compound is administered orally at the appropriate dose(s) and followed 30 minutes later by the insertion of a single 3 mm glass bead 2 cm into the distal colon of each mouse. Mice are marked for identification and placed in large glass beakers for observation. The time required for expulsion of the bead is noted for each mouse with a cut-off period of 30 minutes. Mice not expelling the bead by that time are sacrificed in a carbon dioxide chamber and necropsied to confirm the presence of the bead within the lumen of the colon. Mice for which bead localization within the lumen could not be confirmed (perforation) were not included in the results. Mice receiving vehicle usually expel the bead in a range of 4–6 minutes. Experimental compounds are racemic cisapride, (+) cisapride and (−) cisapride.

Data are analyzed for difference from vehicle control using two-way analysis of variance and Fisher's least significant difference comparision (LSD) test. $ED_{50}s$ (the dose causing a 50% prolongation of time for expulsion) for compounds having significant activity are calculated using regression analysis.

5.7 Example 7

Gastric Emptying

Gastric emptying is evaluated by determining the emptying of 1 mm polystyrene beads from the stomach of fasted rats. Evaluation of gastric emptying in the rat is an important pharamacological parameter. Drug induced inhibition of gastric emptying in the rat is often a characteristic of compounds producing emesis or other gastrointestinal symptoms in other species. Drugs speeding gastric emptying can be useful therapeutically for a number of gastrointestinal dysfunctions. This test is sensitive to the inhibition of gastric emptying produced by anticholinergics and some centrally acting compounds, and to the prokinetic activity of compounds such as metoclopramide, domperidone and racemic cisapride.

Male or female Sprague-Dawley rats, 80–150 grams, are obtained and quarantined for 7 days. They are housed individually on wire with water available ad libitum. Food is withheld 24 hours prior to the study. Rats are administered drug (calculated as base weight) by the appropriate route.

Rats are administered (+), (−), or racemic cisapride by the appropriate route. 30 or 60 minutes later, ten 1 mm polystyrene pellets are administered by garage. For tests evaluating inhibition of gastric emptying, rats are sacrificed 3 hours after pellet administration. To test for potential augmentation of emptying, rats are sacrificed 30 minutes after pellet administration. Rats are sacrificed in a carbon dioxide chamber, and the stomachs are removed. The number of the pellets remaining in the stomach are counted. In control studies, 90% of pellets are still in the stomach after 30 minutes, and fewer than 10% of pellets are in the stomach after 3 hours.

Data are analyzed for difference from vehicle control using two-way analysis of variance and Fisher's least significant difference comparision (LSD) test. $ED_{50}s$ (the dose causing a 50% prolongation of time for expulsion) for compounds having significant activity are calculated using regression analysis.

5.8 Example 8

Central Nervous System Effects

The effects of racemic and optically pure cisapride on memory can be tested using the method described by Forster et al., *Drug Development Research*, 11: 97–106 (1987). In this technique, pharmacologic effects of drugs on memory in mice are tested using a "discriminated escape" paradigm. Groups of mice are designated for vehicle and drug treatment, and each mouse is trained to enter the correct goal arm of a T-maze to escape an 0.8 mA foot shock delivered through the floor of the apparatus. The mice are dosed with vehicle or test compound during the training period.

The mice are initially given a preference trial in which entry to either goal arm will result in termination of foot shock, but they are trained to escape the shock via the arm opposite their preference in all subsequent trials. Mice are trained ("minimal training") until a learning criterion of two consecutive correct choices is met.

One week after training, all mice are tested for retention of the discrimination. The measure of retention is the percentage of correct choice trials, i.e., those in which the mouse enters the arm of the maze in which he does not receive a foot shock. Retention of discrimination is compared for the groups of mice that have been dosed, respectively, with (−) cisapride, (+) cisapride, racemic cisapride, and vehicle.

Effects of racemic and optically pure cisapride on sleep can be tested using electroencephalographic analysis. Groups of rats or dogs are prepared for electroencephalographic recordings by implanting cranial electrodes under general anesthesia, and then connecting these electrodes to an electroencephalic recording device after the effects of the anesthesia have worn off. These recordings are made continuously, and are used to classify the sleep state of the animal. Sleep states are classified as either "awake," "slow-wave sleep," or "REM sleep." The percentage of each of the sleep states following administration of placebo, cisapride isomers, or racemate is compared to evaluate the sleep-regulating effect of the tested drug.

Blockade of the conditioned avoidance response (CAR) can be used to demonstrate the ability of racemic and optically pure cisapride to treat the symptoms of schizophrenia. This testing procedure employs rats that are trained to avoid a foot shock by pressing a lever at the start of a test period. The start of the test period is signaled by a non-noxious stimulus (light or buzzer). Animals that are fully trained in this procedure will avoid the foot shock more than 90% of the time. Compounds that are effective antipsychotics will block this conditioned avoidance response. Thus, (+), (−), and racemic cisapride are tested by administering fixed doses of test and reference compounds to trained rats and then determining their relative effects on conditioned avoidance.

Racemic and optically pure cisapride are tested for antidepressant activity using the mouse tail suspension test (Steru et al., *Psychopharmacology* 85: 367–370, 1985). A fixed dose of (+), (−), or racemic cisapride or a reference drug is administered to a mouse, and the mouse is suspended about 15 cm above the table from a hook that is taped to the tail. The animal's movements are recorded on a polygraph. Mice typically struggle for a few minutes, and then bouts of movement are interspersed with periods of immobility ("behavioral despair"). A decrease in the total duration of immobility during a standard test session signifies potential antidepressant activity of the test compound.

Racemic and optically pure cisapride are tested for effects on psychoactive substance use disorders by administering test or reference compound to laboratory animals, e.g., rats, that are trained to press a lever in anticipation of receiving one of a variety of psychoactive substances ("drug self-administration"). Separate animals that have been trained to self-administer cocaine, alcohol, and morphine are employed in this study. Fixed ratios and progressive ratios are used in setting the amount of lever pressing that is required for the animal to receive the substance. (+), (−), and racemic cisapride are administered at fixed doses before the standard self-administration session. A decrease in the number of self-administrations or a reduction in the lever press/ reward ratio indicates that the test compound has utility in treating psychoactive substance use disorders.

5.9 Example 9

Oral Formulation

Tablets

| Formula | Quantity per Tablet in mg. | | |
|---|---|---|---|
| | A | B | C |
| Active Ingredient (+) cisapride | 5.0 | 10.0 | 25.0 |
| Lactose BP | 62.0 | 57.0 | 42.0 |
| Starch BP | 20.0 | 20.0 | 20.0 |
| Microcrystalline Cellulose | 10.0 | 10.0 | 10.0 |
| Hydrogenated Vegetable Oil | 1.5 | 1.5 | 1.5 |
| Polyvinylpyrrolidinone | 1.5 | 1.5 | 1.5 |
| Compression Weight | 100.0 | 100.0 | 100.0 |

The active ingredient, (+) cisapride, is sieved through a suitable sieve and blended with the lactose until a uniform blend is formed. Suitable volumes of water are added and the powders are granulated. After drying,-the granules are then screened and blended with the remaining excipients. The resulting granules are then compressed into tablets of desired shape. Tablets of other strengths may be prepared by altering the ratio of active ingredient to the excipient(s) or the compression weight.

What is claimed is:

1. A method of treating a disorder of the central nervous system, selected from the group consisting of cognitive disorders, behavioral disorders, mood disorders, and disorders of control of autonomic function, in a human, comprising administering to said human a therapetically effective amount of (+) cisapride or a pharmaceutically acceptable salt thereof, substantially free of its (−) stereoisomer.

2. The method of claim 1, wherein said disorder is a behavioral disorders.

3. The method of claim 2, wherein said behavioral disorder is schizophrenia.

4. The method of claim 2, wherein said behavioral disorder is mania.

5. The method of claim 2, wherein said behavioral disorder is obsessive-compulsive disorder.

6. The method of claim 2, wherein said behavioral disorder is a psychoactive substance use disorder.

7. The method of claim 1, wherein said behavioral disorder is a disorder of control of autonomic function.

8. The method of claim 7, wherein said disorder of control of autonomic function is hypertension.

* * * * *